United States Patent

Beckett et al.

[11] Patent Number: 5,861,436
[45] Date of Patent: Jan. 19, 1999

[54] HYDROXAMIC ACID DERIVATIVES AS METALLOPROTEINASE INHIBITORS

[75] Inventors: Raymond Paul Beckett; Mark Whittaker; Andrew Miller, all of Oxford, United Kingdom

[73] Assignee: British Biotech Pharmaceuticals Limited, Oxford, England

[21] Appl. No.: 841,079

[22] Filed: Apr. 29, 1997

Related U.S. Application Data

[63] Continuation of Ser. No. 676,358, filed as PCT/GB95/00120 Jan. 23, 1995 published as WO95/19957 Jul. 27, 1995, abandoned.

[30] Foreign Application Priority Data

Jan. 21, 1994 [GB] United Kingdom ................ 9401129

[51] Int. Cl.$^6$ .................................................. A61K 31/19
[52] U.S. Cl. .................... 514/575; 562/801; 562/621; 562/622
[58] Field of Search ............................ 514/575; 562/801, 562/621, 622

[56] References Cited

U.S. PATENT DOCUMENTS

| | | | |
|---|---|---|---|
| 3,468,936 | 9/1969 | van der Burg | 260/500.5 |
| 4,996,358 | 2/1991 | Handa et al. | 562/621 |
| 5,183,900 | 2/1993 | Galardy et al. | 548/495 |
| 5,300,674 | 4/1994 | Crimmin et al. | 560/42 |
| 5,304,549 | 4/1994 | Broadhurst et al. | 514/80 |

FOREIGN PATENT DOCUMENTS

| | | |
|---|---|---|
| 0236872 | 9/1987 | European Pat. Off. . |
| 0497192 | 1/1992 | European Pat. Off. . |
| 0575844 | 12/1993 | European Pat. Off. . |
| 2268933 | 1/1994 | United Kingdom . |
| 9402247 | 2/1993 | WIPO . |
| 9519961 | 7/1995 | WIPO . |
| 9402446 | 2/1998 | WIPO . |

*Primary Examiner*—Brian M. Burn
*Attorney, Agent, or Firm*—Hale and Dorr LLP

[57] ABSTRACT

The present invention relates to therapeutically active hydroxamic acid derivatives, to pharmaceutical compositions containing them, and to the therapeutic use of these compounds. In particular, the compounds are inhibitors of matrix metalloproteinases that are involved in tissue degradation, and in addition, are inhibitors of the release of tumor necrosis factor from cells.

7 Claims, No Drawings

HYDROXAMIC ACID DERIVATIVES AS METALLOPROTEINASE INHIBITORS

This application is a continuation, of application Ser. No. 08/676,358, filed 22 Jul. 1996, now abandoned, which is a Section 371 of PCT/GB95/00120, filed 23 Jan. 1995.

The present invention relates to therapeutically active hydroxamic acid derivatives, to processes for their preparation, to pharmaceutical compositions containing them, and to the use of such compounds in medicine. In particular, the compounds are inhibitors of metalloproteinases involved in tissue degradation, and in addition are inhibitors of the release of tumour necrosis factor from cells.

BACKGROUND OF THE INVENTION

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth.

Tumour necrosis factor (herein referred to as "TNF") is a cytokine which is produced initially as a cell-associated 28kD precursor. It is released as an active. 17kD form . which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Compounds which inhibit the production or action of TNF are therefore thought to be potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Since excessive TNF production has been noted in several diseases or conditions also characterised by MMP-mediated tissue degradation, compounds which inhibit both MMPs and TNF production may have particular advantages in the treatment or prophylaxis of diseases or conditions in which both mechanisms are involved.

Several classes of MMP inhibitors have been proposed, including derivatives of hydroxamic acid. The following patent publications disclose hydroxamic acid-based MMP inhibitors:

US 4599361 (Searle)
EP-A-0236872 (Roche)
EP-A-0274453 (Bellon)
WO 90/05716 (British Bio-technology)
WO 90/05719 (British Bio-technology)
WO 91/02716 (British Bio-technology)
EP-A-0489577 (Celltech)
EP-A-0489579 (Celltech)
EP-A-0497192 (Roche)
WO 92/13831 (British Bio-technology)
WO 92/22523 (Research Corporation Technologies)
WO 93/09090 (Yamanouchi)
WO 93/09097 (Sankyo)
WO 93/20047 (British Bio-technology)
WO 93/24449 (Celltech)
WO 93/24475 (Celltech)
EP-A-0574758 (Roche)

The intrinsic potency of compounds within the broad structural groups of hydroxamic derivatives disclosed in the above publications against particular MMPs can be high. For example, many have a collagenase $IC_{50}$ by the in vitro test method of Cawston and Barrett, (Anal. Biochem., 99, 340–345, 1979) of less than 50 nM. Unfortunately, however, the physicochemical and/or pharmacokinetic properties of the specific compounds disclosed in those publications have generally been disappointing. Identifying hydroxamic acid-based MMP inhibitors having a good balance of high intrinsic activity against the target MMPs, and good physicochemical and/or pharmacokinetic properties, such that the compounds are easily formulated for administration, have good bioavailability for acceptable periods following administration, and have high in vivo activity in the target disease or condition, remains a much sought after goal in the art.

The hydroxamic acid derivatives disclosed in the above publications can be regarded as having the following basic structure (IA):

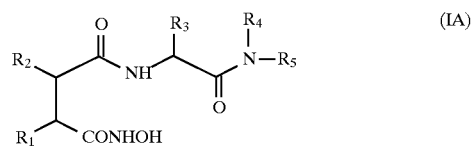

wherein the five substituents $R_1$–$R_5$ may vary according to the detailed disclosure of each publication. The balance of intrinsic level of activity, degree of specificity of inhibition of particular categories of MMP, physicochemical and pharmacokinetic properties can vary in an unpredictable way as the substituents $R_1$–$R_5$ are varied.

Of the above publications, only EP-A-0236872 refers to the possibility that in a particular class of collagenase inhibitors of basic structure (lA) the substituent $R_1$, may be OH. That possibility is referred to amongst many other possible $R_1$. substituents, in the context of compounds in which the substituent $R_3$ is the characteristic side chain of a naturally occurring amino acid in which any functional substituents may be protected, any amino group may be acylated, and any carboxyl group may be esterified. EP-A-0236872 does not disclose such compounds as having preferred or particularly advantageous collagenase inhibitory properties, and in fact contains no disclosure of any specific compound in which $R_1$. is hydroxy. It does not address the problem in the art referred to above of providing hydroxamic acid derived MMP inhibitors having the elusive balance of good intrinsic activity profile and good physicochemical and pharmacokinetic properties.

Brief Description of the Invention

Our patent application PCT/G893/01557 discloses a novel group of compounds of general formula (lA), principally characterised in that the $R_1$ substituent is a hydroxy group and in which the selected substituent $R_3$ is not the side chain of a natural amino acid. It discloses that such compounds have in general the sought after but unpredictable combination of desirable formulation characteristics, including good water-solubility, as well as desirable activity profiles as inhibitors of MMP's, including both collagenase and stromelysin inhibitory activity. It states that the class includes compounds which achieve high serum levels following oral administration, and which are active in vivo following oral administration in relevant animal models of diseases and conditions mediated by MMP's. Furthermore, the, compounds are stated to have the unexpected and desirable property of inhibiting TNF production.

This invention relates to compounds falling within the general disclosure of PCT/GB93/01557, and having the properties and advantages therein referred to, but not specifically disclosed therein.

DETAILED DESCRIPTION OF THE INEVNTION

The present invention provides a compound which is a member of the group consisting of:

1. 2S-Hydroxy-3R-[1S-(tert-butylcarbamoyl)-2,2-dimethyl-propylcarbamoyl]-5-methyl-hexanohydroxamic acid,
2. 2S-Hydroxy-3R-[1S-(N,N-dimethylcarbamoyl)-2,2-dimethyl-propyl-carbamoyl]-5-methyl-hexanohydroxamic acid,
3. 2S-Hydroxy-3R-[1S-(3-hydroxy-2,2-dimethylpropylcarbamoyl)-2.2-dimethyl-propylcarbamoyl]-5-methyl-hexanohydroxamic acid,
4. 2S-Hydroxy-3R-[1S-(methylcarbamoyl)-2,2-dimethyl-propylcarbamoyl]-6-phenyl-hexanohydroxamic acid,
5. 2S-Hydroxy-3R-[1S-(methylcarbamoyl)-2,2-dimethyl-butylcarbamoyl]-5-methyl-hexanohydroxamic acid, and salts, solvates or hydrates thereof. Similar compounds to those provided by the present invention include:

2S-Hydroxy-3R-[1S-(3-methoxy-2,2-dimethylpropylcarbamoyl)-2,2-dimethyl-propylcarbamoyl]-5-methyl-hexanohydroxamic acid, 2S-Hydroxy-3R-[1S-(methylcarbamoyl)-2.2-dimethyl-propylcarbamoyl]-6-(4-chloro)phenyl-hexanohydoxamic acid.

2S-Hydroxy-3R-[1S-(methylcarbamoyl)-2,2-dimethyl-propylcarbamoyl]-octanohydroxamic acid, 2S-Hydroxy-3R-[1S-(pyridin-2-ylmethylcarbamoyl)-2,2-dimethyl-propylcarbamoyl]-5-methyl-hexanohydroxamic acid, 2S-Hydroxy-3R-[1S-(pyridin-3-ylmethylcarbamoyl)-2,2-dimethyl-propylcarbamoyl]-5-methyl-hexanohydroxamic acid, 2S-Hydroxy-3R-[1S-(pyridin-4-ylmethylcarbamoyl)-2,2-dimethyl-propylcarbamoyl]-5-methyl-hexanohydroxamic acid, 2S-Hydroxy-3R-[1S-(methylcarbamoyl)-2,2-dimethyl-propylcarbamoyl]-4-methoxy-butanohydroxamic acid, 2S-Hydroxy-3R-[1S-(methylcarbamoyl)-2.2-dimethyl-propylcarbamoyl]-4-benzyloxy-butanohydroxamic acid, 2S-Hydroxy-3R-[1S-(methylcarbamoyl)-2,2-dimethyl-propylcarbamoyl]-4-benzylthio-butanohydroxamic acid, and 2S-Hydroxy-3R-[1S-(methylcarbamoyl)-2,2-dimethyl-buten-3-ylcarbamoyl]-5-methyl-hexanohydroxamic acid, and salts, solvates or hydrates thereof.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

As mentioned above, compounds of the invention are useful in human or veterinary medicine since they are active as inhibitors of MMPs, and a further advantage lies in their ability to inhibit the release of tumour necrosis factor (TNF) from cells.

Accordingly in another aspect, this invention concerns:

(i) a method of management (by which is meant treatment or prophylaxis) of diseases or conditions mediated by MMPs and/or TNF in mammals, in particular in humans, which method comprises administering to the mammal an effective amount of a compound of the invention, or a pharmaceutically acceptable salt thereof; and (ii) a compound of the invention for use in human or veterinary medicine, particularly in the management (by which is meant treatment or prophylaxis) of diseases or conditions mediated by MMPs and/or TNF; and (iii) the use of a compound of the invention in the preparation of an agent for the management (by which is meant treatment or prophylaxis) of diseases or conditions mediated by MMPs and/or TNF.

Diseases or conditions mediated by MMPs include those involving tissue breakdown such as bone resorption, inflammatory diseases, dermatological conditions and tumour invasion by secondary metastases, in particular rheumatoid arthritis, osteoarthritis, periodontitis, gingivitis, corneal ulceration and tumour invasion by secondary metastases. Diseases or conditions mediated by TNF include inflammation, fever, cardiovascular effects, haemorrhage, coagulation and acute phase response, cachexia and anorexia, acute infections, shock states, graft versus host reactions and autoimmune disease.

In a further aspect of the invention there is provided a pharmaceutical or veterinary composition comprising a compound of the invention together with a pharmaceutically or veterinarily acceptable excipient or carrier. In view of the water-solubility, and oral bioavailability advantanges of compounds in accordance with the invention, a further aspect of the invention comprises a pharmaceutical or veterinary composition comprising a compound of the invention together with a pharmaceutically or veterinarily acceptable excipient or carrier, characterised in that the composition is adapted for oral administration.

One or more compounds of the invention may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica: disintegrants for example potato starch. or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p- hydroxybenzoate or sorbic acid, and if desired conventional flavouring or colouring agents.

The dosage unit involved in oral administration may contain from about 1 to 250 mg, preferably from about 25 to 250 mg of a compound of the invention. A suitable daily dose for a mammal may vary widely depending on the condition of the patient. However, a dose of a compound of general formula 1 of about 0.1 to 300mg/kg body weight, particularly from about 1 to 100mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite os disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint. The daily dosage for a 70 kg mammal may be in the range 10 mgs to 1 gram.

The following Examples disclose the preparation of the compounds of the invention:

The amino acids used in the examples below were commercially available or were prepared according to literature procedures. In all cases these were converted to the required N-methylamides by standard methods.

The following abbreviations have been used throughout:

| | |
|---|---|
| DIPE | Diisopropyl ether |
| DMF | N,N-Dimethylformamide |
| EDC | N-Ethyl-N'-(3-dimethylaminopropyl)carbodiimide hydrochloride |
| HOBt | 1-Hydroxybenzotriazole |
| LDA | Lithium N,N-diisopropylamide |
| NMM | N-Methylmorpholine |
| THF | Tetrahydrofuran |
| TFA | Trifluoroacetic acid |
| TLC | Thin layer chromatography |

$^1$H and $^{13}$C NMR spectra were recorded using a Bruker AC 250 E spectrometer at 250.1 and 62.9 MHz, respectively. Elemental microanalyses were performed by CHN Analysis Ltd. (Alpha House, Countesthorpe Road, South Wigston, Leicester LE8 2PJ, UK) or Medac Ltd. (Department of Chemistry, Brunel University, Uxbridge, Middlesex UB8 3PH).

Example 1

2S-Hydroxy-3R-(1S-tert-butylcarbamoyl]-2,2-dimethyl-propylcarbamoyl)-5-methyl-hexanohydroxamic acid

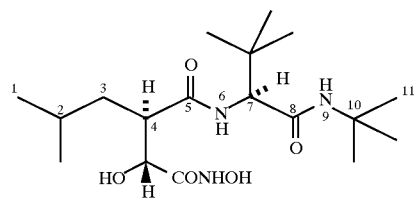

STEP A: 2S-Hydroxy-3R-isobutenyl-butan-1,4-dioic acid diisopropyl ester

2S-Hydroxybutan-1,4-dioic acid diisopropyl ester (50 g, 230 mmol) was added to a solution of LDA [from N,N-diisopropylamine (80 ml, 570 mmol) and 10 M n-butyllithium (48.1 ml, 481 mmol)] in dry THF (500 ml) whilst maintaining the temperature at –70° C. When addition was complete the reaction was warmed to –15° C. and stirred for 8 hours. The reaction mixture was cooled to –70° C. and methallyl iodide (46 g, 252 mmol) was added slowly, ensuring that the temperature did not exceed –65° C. The mixture was warmed to –40° C. and stirred for 18 hours before quenching at –15° C. with citric acid. The organic layer was separated and washed with 10% NaHCO$_3$ solution (500 ml) and brine (300 ml) then dried (MgSO$_4$). The solution was filtered and concentrated in vacuo to give a brown oil (64 g) which was purified by column chromatography (silica gel, 1 kg, gradient elution with 20 to 35% diethyl ether in hexane). The desired product was isolated as a colourless oil (30.9 g, 49%) which was found to be a 17:1 mixture of diastereomers by NMR. $^1$H-NMR; $\delta$(CDCl$_3$, major diastereomer). 5.06 (1H. septet. J=6.3 Hz), 4.97 (1H, septet, J=6.3 Hz), 4.78 (2H, d, J=7.1 Hz), 4.16 (1H. m). 3.20(1 H, d, J=6.2 Hz), 3.00 (1 H, m), 2.50, 2.35 (2H, ABX, J=7.0, 8.7, 14.4 Hz) 1.72 (3H. s) and 1.24-1.16 (12H, 2m).

STEP B: 2S-Hydroxy-3R-isobutyl-butan-1,4-dioic acid diisopropyl ester

2S-Hydroxy-3R-isobutenyl-butan-1,4-dioic acid diisopropyl ester (7.14 g, 26.2 mmol) was dissolved in ethanol (80 ml), and stirred overnight with 10% palladium on charcoal catalyst (1.0 g) under an atmosphere of hydrogen. The catalyst was removed by filtration and the filtrate was evaporated to dryness to leave the product as a clear oil (7.03 g, 98%). 1H-NMR; δ (CDCl$_3$), 5.06 (1H, septet, J=6.3 Hz), 4.97(1H, septet, J=6.3 Hz), 4.17 (1 H, br s,), 3.24 (I H. br s), 2.83 (1 H, m), 1.68 (2H, m), 1.44 (1H, m), 1.24 (6H, d, J=6.2 Hz), 1.18 (6H, d, J=6.2 Hz) and 0.89 (6H, m).

STEP C: 2S-Hydroxy-3R-isobutenyl-butan-1,4-dioic acid

2S-Hydroxy-3R-isobutyl-butan-1,4-dioic acid diisopropyl ester (7.0 g. 25.6 mmol) was dissolved in dioxane (15 ml) and water (15 ml), a solution of KOH (4.29 g) in water (22 ml) was added and the mixture was heated at 90° C. overnight. The solution was allowed to cool and then passed through an ion exchange resin (Dowex 50×4–400, 200 ml) and evaporated to yield the title compound (4.82 g, 99%). $^1$H-NMR; δ(CDCl$_3$), 8.70 (2H, br s), 4.32 (1 H, br s), 3.10 (1 H, m), 1.85–1.55 (3H, m) and 0.96 (6H, m).

STEP D: 2R-(2,2-Dimethyl-4-oxo-1,3-dioxalan-5S-yl)-4-methylpentanoic acid

2S-Hydroxy-3R-isobutyl-butan-1,4-dioic acid (5.19 g, 27.3 mmol) was dissolved in 2,2-dimethoxypropane (150 ml) and DMF (40 ml) and stirred overnight at 30° C. in the presence of a catalytic amount of p-toluene sulphonic acid. The solvent was removed to give the title compound contaminated with solvent (6.87 g, crude). $^1$H-NMR; δ(CDCl$_3$), 4.41 (1H, d, J=4.8 Hz), 2.91 (1 H, m), 1.69 (3H, m), 1.54 (3H, s), 1.48 (3H, s) and 0.88 (6H, m).

STEP E: 2R-(2,2-Dimethyl-4-oxo-1,3-dioxalan-5S-yl)-4-methyl-pentanoic acid pentafluorophenyl ester 2R-(2,2-Dimethyl-4-oxo-1,3-dioxalan-5S-yl)-4-methylpentanoic acid (558 mg, 2.4 mmol) was taken up in dichloromethane (10 ml) and cooled to 0° C. before adding pentafluorophenol (670 mg, 3.6 mmol) and EDC (560 mg, 2.9 mmol). The reaction was stirred at 0° C. for 2 hours then the solution was washed with 1M sodium carbonate (50 ml) and brine (20 ml). The organic layer was dried (magnesium sulphate), filtered, evaporated to dryness and purified by column chromatography (silica gel, dichloromethane) to give the activated ester (552 mg, 58%). 1H-NMR; δ(CDCl$_3$), 4.57 (1H, d, J=6.5 Hz), 3.32 (1H, m), 1.86 (3H, m), 1.67 (3H, s), 1.58 (3H, s) and 1.03 (6H, m).

STEP F: N$^a$-tert-Butyloxycarbonyl-L-tert-leucine-N-teft-butylamide

N$^a$-tert-Butyloxycarbonyl-L-tert-leucine (15.60 g, 72.5 mmol) was dissolved in dichloromethane (200 ml) and the solution was cooled to 0° C and stirred during the addition of pentafluorophenol (14.67 g, 79.7 mmol), followed by EDC (15.28 g, 79.7 mmol). The mixture was allowed to warm to room temperature, stirred for a further 1 hour then cooled back to 0° C. tert-Butylamine (13.2 g, 181.2 mmol) was added dropwise and the mixture was warmed to room temperature then stirred for a further 3 hours. The white solid that was formed was collected by filtration, dissolved in dichloromethane and washed successively with 1M Na$_2$CO$_3$, 1M HCl and finally with brine before drying over anhydrous MgSO$_4$. The solution was filtered and evaporated to an oil which crystallised on trituration with hot ethyl acetate. The mixture was cooled and the solid was collected by filtration and washed with cold ethyl acetate. Yield: 8.04 g (41%). 1H-NMR; δ(CDCl$_3$), 5.47 (1H, s), 5.21 (1 H, br d), 3.64 (1H, d, J=9.3 Hz), 1.42 (9H, s), 1.33 (9H, s), 0.97 (9H, s).

STEP G:

L-tert-Leucine-N-tert-butylamide trifluoroacetate salt

The product from Example if (8.00 g, 27.9 mmol) was dissolved in dichloromethane (7 ml) and TFA (7 ml) and stored at 4° C. overnight. The solvents were removed under reduced pressure and the residue was triturated with diethyl ether. The resulting white precipitate was collected by filtration, washed with more diethyl ether and dried under high vacuum. Yield: 7.31 g (87%). 1H-NMR; δ(CD$_3$OD), 3.45 (1 H, s), 1.37 (9H, s), 1.05 (9H, s).

STEP H:

N$^a$-2R-(2,2-Dimethyl-4-oxo-1,3-dioxalan-5S-yl)-4-methylpentanoyl]-L-tert-leucine-N-tert-butylamide The product from Example 1 g (3.60 g, 12.0 mmol) was dissolved in DMF (2 ml) and the solution was cooled to 0° C. and stirred during the addition of NMM (1.21 g, 12.0 mmol). After a further 10 minutes, 2R-(2,2-dimethyl-4-oxo-1,3-dioxalan-5S-yl)-4-methylpentanoic acid pentafluorophenyl ester (Example 1e) (5.0 g, 12.6 mmol), was added. The reaction mixture was stirred for 30 minutes at 0° C. then for 60 hours at room temperature. The solvent was removed under reduced pressure and the residue was taken up in dichloromethane and washed with 1M Na$_2$CO$_3$ and brine. The organic phase was dried (MgSO$_4$), filtered and evaporated to leave a white solid which was triturated with hexane and collected by filtration. Yield: 3.36 g (70%). 1H-NMR; δ(CDCl$_3$), 6.44 (1H, d, J=8.7 Hz), 5.46 (1H, s), 4.46 (1H, d, J=6.5 Hz). 4.03 (1 H, d. J=9.3 Hz), 2.70 (1 H, m), 1.75 (1 H, m), 1.64 (2H, m), 1.62 (3H, s), 1.52 (3H, s), 1.33 (9H, s), 1.00 (9H, s), 0.92 (3H, d, J=6.2 Hz), 0.90 (3H, d, J=6.3 Hz).

STEP I:

2S-Hydroxy-3R-(1S-tert-butlylcarbamoyl-2,2-dimethyl-propylcarbamoyl)-5-methyl-hexanohydroxamic acid Hydroxylamine hydrochloride (2.32 g, 33.5 mmol) was dissolved in methanol (50 ml), anhydrous sodium methoxide (1.81 g, 33.5 mmol) was added and the mixture was stirred for 2 hours at room temperature. The residual solid was removed by fltration and the filtrate was added dropwise with stirring to a cooled (0° C.) solution of N$^2$-[2R-(2R-(2,2-dimethyl-4-oxo-1,3-dioxalan-5S-yl)-4-methylpentanoyl]-L-tert-leucine-N$^1$-tert-butylamide (3.33 g, 8.4 mmol) in a minimum volume of methanol. The solution was stirred for 10 minutes at 0° C. then overnight at room temperature. The solvent was removed under reduced pressure and the residue was partitioned between diethyl ether (60 ml) and water (15 ml). The organic phase was separated, dried (MgSO$_4$), filtered and evaporated to a solid, which was combined with product from a smaller scale (5.2 mmol) reaction. Column chromatography (acid-washed silica, gradient elution with 5% methanol in dichloromethane) then afforded the title compound as a white solid. Yield: 2.49 g (71%). 1H-NMR; δ(CD$_3$OD), 4.16 (1 H, s), 3.98 (1 H, d, J=6.5Hz), 2.82 (1 H. m), 1.55 (2H, br m), 1.29 (9H, s), 1.22 (1 H, m), 0.96 (9H, s), 0.89 (3H, d, J=6.4Hz), and 0.85 (3H, d, J=6.4Hz). $^{13}$C-NMR: δ(CDCl$_3$), 174.7, 169.7, 168.7, 72.8, 61.3, 51.7, 45.5, 39.2, 34.7, 28.5, 26.7, 25.8, 22.8 and 22.2. Found: C 57.38, H 9.35, N 10.78%; C$_{18}$H$_{35}$N$_3$O$_5$.0.2 H$_2$O requires: C 57.33, H 9.46, N 11.14%.

Example 2

2S-Hydroxy-3R-[1S-(N,N-dimethylcarbamoyl)-2,2-dimethyl-propylcarbamoyl]-5-methyl-hexanohydroxamic acid

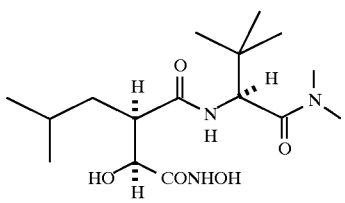

Prepared by methods analogous to those described in Example 1. $^{1}$H-NMR: δ(CD$_3$OD), 4.85 (1H, s), 4.01 (1H, d, J=5.6Hz), 3.14 (3H, s), 2.90 (3H, s), 2.83 (1H, m), 1.59 (1H, m), 1.50 (1H, m), 1.28 (1H, m), 0.97 (9H, s), and 0.87 (6H, m). $^{13}$C-NMR; d (CD$_3$OD), 175.6, 173.2, 171.4, 73.2, 56.1, 56.0, 49.3, 39.8, 38.9, 36.3, 36.1, 27.0, 23.5 and 22.5. Found: C 55.11, H 8.92, N 12.06%; C$_{16}$H$_{31}$N$_3$O$_5$.0.2 H$_2$O requires: C 55.06, H 9.07, N 12.04%.

Example 3

2S-Hydroxy-3R-{1S-[3-hydroxy-2,2-dimethylpropylcarbamoyl]-2.2-dimethyl-propylcarbamoyl}-5-methyl-hexanohydroxamic acid

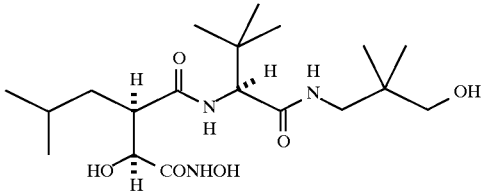

Prepared by methods analogous to those described in Example 1. $^{1}$H-NMR; δ(CD$_3$OD), 4.23 (1 H, s), 3.99 (1 H, d, J=6.3Hz), 3.16 (2H, s), 3.11 (1H, d, J=13.7Hz), 2.95 (1H, d. J=13.6Hz), 2.81 (1H, m), 1.60 (1H, m), 1.47 (1H, m), 1.22 (1 H, m), 0.98 (9H, s), 0.89 (3H, d, J=6.4Hz), 0.85 (3H, d, J=6.4Hz), 0.84 (3H, s), and 0.82 (3H, s). $_{13}$C-NMR; δ((CD$_3$)$_2$SO), 172.3, 171.0, 168.8, 71.4, 67.8, 60.0, 47.8, 45.3, 37.3, 36.6, 34.0, 26.7, 25.3, 23.6, 22.3, 22.3 and 21.7. Found: C 56.37, H 9.32, N 9.97%; C$_{19}$H$_{37}$N$_3$O$_6$. . 0.2 H$_2$O requires: C 56.30, H 9.25. N 10.37%.

Example 4

2S-Hydroxy-3R-[1S-(methylcarbamoyl)-2,2-dimethyl-propylcarbamoyl]-6-phenyl-hexanohydroxamic acid

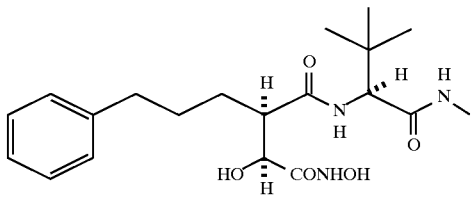

Prepared by methods analogous to those described in Example 1. White solid. $^{1}$ H-NMR; δ((CD$_3$)$_2$SO), 8.86 (1H, br s), 7.91 (1H, d, J=4.3Hz). 7.61 (1H, d, J=9.4Hz), 7.27–7.12 (6H, m), 5.39 (1H, d, J=7.4Hz), 4.21–4.17 (1H, m), 3.83–3.77 (1 H, m), 2.69–2.44 (6H, m), 1.48–1.27 (4H, m), and 0.90 (9H, s), $^{13}$C-NMR; δ((CD$_3$)$_2$SO), 172.3, 170.5, 168.9, 142.1, 128.1, 125.5, 71.1, 60.0. 49.3. 35.7, 35.1, 28.8, 28.3. 26.9 and 25.2.

Example 5

2S-Hydroxy-3R-[l1S-(methylcarbamoyl)-2,2-dimethyl-butylcarbamoyl]-5-methyl-hexanohydroxamic acid

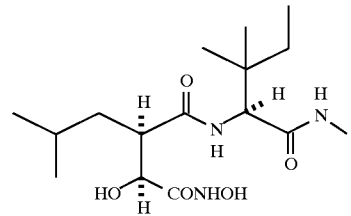

Prepared by methods analogous to those described in Example 1 starting from the racemic amino acid derivative N-benzyloxycarbonyl-D,L-3-ethylvaline (obtained from Kiralchem Ltd, 17 Canalside, 2–4 Orsman Road, London N1 5JQ). The diastereomeric acetonides were separated following Step H and converted individually to the hydroxamic acids below:

SRS Diastereoisomer (Preferred stereochemistry): White solid. 181–181.5° C. $^{1}$H-NMR; δ(CD$_3$OD), 7.89 (1H, d, J=4.1 Hz), 7.72 (1H, d, J=9.0Hz), 4.16 (1H, m), 4.00 (IH, d, J =5.5 Hz), 2.77–2.69 (1H, m), 2.61 (3H, d, J=4.4 Hz), 1.58–1.19 (2H, m), 1.17–1.09 (3H, m) and 0.85–0.72 (15H, m), $^{13}$C-NMR; δ(CD$_3$OD), 175.5, 173.4, 171.6, 72.9, 80.8, 49.5, 39.9, 37.9, 32.9, 26.9, 26.1, 23.7, 23.6, 22.4 and 8.5. IR (KBr disc); V$_{max,}$ 3270, 2954, 1659, 1523, 1382 cm$^1$ .

SRR Diastereoisomer: White solid. m.p. 182° C. $^{1}$ H-NMR; δ(CD$_3$OD), 7.80 (1 H, d, J=8.8 Hz), 7.68 (1H, d, J=4.6 Hz), 4.14 (1H, m), 3.86 (1H, d, J=7.7 Hz), 2.87–2.78 (1H, m), 2.58 (3H, d, J=4.6 Hz), 1.60–1.20 (4H, m), 1.08–0.95 (1H, m) and 0.89–0.72 (15H, m). $^{13}$C-NMR; δ(CD$_3$OD), 175.9, 173.6, 171.4, 73.6, 61.1, 49.1, 38.5, 37.4, 33.3, 27.1, 26.1, 24.2, 24.0, 23.9, 22.0 and 8.5. Found: C 50.31, H 9.11, N, 10.97%; C$_{16}$H$_{31}$N$_3$ $_{O5}$. 2.0 H$_2$O requires: C 50.38, H 9.25, N 11.02% IR (KBr disc): V$_{max}$, 3303, 2954, 1643, 1534 cm$^1$.

Examples 6–15

Employing analogous methods to those used in Examples 1–5 the compounds of Examples 6–15 are prepared from the appropriate starting materials. 6. 2S-Hydroxy-3R-[1S-(3-methoxy-2,2-dimethylpropylcarbamoyl)-2,2-dimethyl-propylcarbamoyl]-5-methyl-hexanohydroxamic acid, 7. 2S-Hydroxy-3R-[1S-(methylcarbamoyl)-2,2-dimethyl-propylcarbamoyl]-6-(4-chloro)phenyl-hexanohydoxamic acid, 8. 2S-Hydroxy-3R-[1S-(methylcarbamoyl)-2,2-dimethyl-propylcarbamoyl]-octanohydroxamic acid, 9. 2S-Hydroxy-3R-[1S-(pyridin-2-ylmethylcarbamoyl)-2.2-dimethyl-propylcarbamoyl]-5-methyl-hexanohydroxamic acid, 10. 2S-Hydroxy-3R-[1S-(pyridin-3-ylmethylcarbamoyl)-2,2-dimethyl-propylcarbamoyl]-5-methyl-hexanohydroxamic acid, 11. 2S-Hydroxy-3R-[1S-(pyridin-4-ylmethylcarbamoyl)-2,2-dimethyl-propylcarbamoyl]-5-methyl-hexanohydroxamic acid, 12. 2S-Hydroxy-3R-[1S-(methylcarbamoyl)-2,2-dimethyl-propylcarbamoyl]-4-methoxy-butanohydroxamic acid, 13. 2S-Hydroxy-3R-[1S-(methylcarbamoyl)-2,2-dimethyl-propylcarbamoyl]-4-benzyloxy-butanohydroxamic acid, 14. 2S-Hydroxy-3R-[1S-(methylcarbamoyl)-2,2-dimethyl-propylcarbamoyl]-4-benzylthio-butanohydroxamic acid, and 15. 2S-Hydroxy-3R-(1S-(methylcarbamoyl)-2,2-dimethyl-buten-3-ylcarbamoyl]-5-methyl-hexanohydroxamic acid.

We claim:

1. A compound which is a member of the group consisting of:

2S-Hydroxy-3R-[1S-(tert-butylcarbamoyl)-2,2-dimethyl-propylcarbamoyl]-5-methyl-hexanohydroxamic acid, 2S-Hydroxy-3R-[1S-(N,N-dimethylcarbamoyl)-2,2-dimethyl-propyl-carbamoyl]-5-methyl-hexanohydroxamic acid, 2S-Hydroxy-3R-[1S-(3-hydroxy-2,2-dimethylpropylcarbamoyl)-2,2-dimethyl-propylcarbamoyl]-5-methyl-hexanohydroxamic acid, 2S-Hydroxy-3R-[1S-(methylcarbamoyl)-2,2-dimethyl-propylcarbamoyl)-6-phenyl-hexanohydroxamic acid, 2S-Hydroxy-3R-[1S-(methylcarbamoyl)-2,2-dimethyl-butylcarbamoyl]-5-methyl-hexanohydroxamic acid.

and salts, solvates or hydrates thereof.

2. A pharmaceutical composition comprising the compound of claim 1 and a pharmaceutically or veterinarily acceptable excipient or carrier.

3. The pharmaceutical composition of claim 2 wherein said pharmaceutical composition is administered orally.

4. A method of inhibiting NMP activity comprising administering an effective amount of the compound of claim 1.

5. The method of claim 4, wherein said MMP activity is the result of a patient suffering from, or as a prophylaxis for, rheumatoid arthritis, osteoarthritis, periodontitis, gingivitis, corneal ulceration or tumor invasion by secondary metastases.

6. A method of inhibiting TNF activity comprising administering an effective amount of the compound of claim 1.

7. The method of claim 6 wherein inhibiting said TNF activity is the result of a patient suffering from, or as a prophylaxis for, inflammation, fever, cardiovascular effects, haemorrhage, coagulation and acute phase response, cachexia and anorexia, an acute infection, a shock state, a graft versus host reaction, or autoimmune disease.

* * * * *